United States Patent [19]

Patel et al.

[11] Patent Number: 5,616,593

[45] Date of Patent: Apr. 1, 1997

[54] COMPOSITIONS CONTAINING PIPERINE

[75] Inventors: Ramanbhai B. Patel; Indravadan A. Modi, both of Ahmedabad, India

[73] Assignee: Cadila Laboratories Limited, Ahmedabad, India

[21] Appl. No.: 324,584

[22] Filed: Oct. 18, 1994

[30] Foreign Application Priority Data

Oct. 29, 1993 [IN] India ............................. 356/BOM/93

[51] Int. Cl.$^6$ ..................................................... A01N 43/40
[52] U.S. Cl. ................................................ 514/321; 514/328
[58] Field of Search ..................................... 514/321, 328

[56] References Cited

PUBLICATIONS

Johri, R. K, et al., "An Ayurevdic formulation 'Trikatu' and its constituants", *Journal of Ethnopharmacology*, vol. 37 1992 pp. 85–91.

Zutshi, R.K, et al., "Influence of Piperine on . . . Tuberculosis", *Journal of Physicians India*, vol. 33 pp. 223–224 1985.

Bano, G., et al., "Effect of Piperine on . . . Healthy Volunteers" *European Journal of Clinical Pharmacology*, vol. 41, No. 6 1991, pp. 615–617.

CA 95:156487 (1981).

*Primary Examiner*—Paul J. Killos
*Attorney, Agent, or Firm*—Ladas & Parry

[57] ABSTRACT

A pharmaceutical composition having increased bioavailability characterized by piperine of the formula

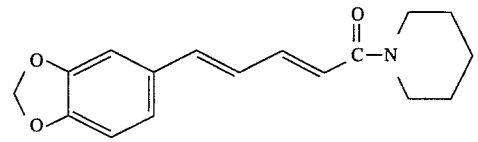

and a drug for treating a disease or condition of the human cardiovascular system, central nervous system, gastrointestinal tract, respiratory tract, endocrine system, genito urinary tract or haemopoietic system.

13 Claims, No Drawings

COMPOSITIONS CONTAINING PIPERINE

The present invention relates to a pharmaceutical composition having increased therapeutic efficacy. More particularly, the invention relates to a pharmaceutical composition containing piperine as a bio-availability enhancer. The composition of the present invention is useful for the treatment of diseases which affect the cardiovascular, central nervous, gastro-intestinal, respiratory, endocrine, genito-urinary and haemopoietic systems of the human body.

Though many drugs are available in the market for the treatment of diseases that affect these systems, it is useful for effective and non-toxic drugs for the treatment of the diseases to be available at an inexpensive price.

Accordingly, research is being conducted for the development of the drugs in the direction of ascertaining the dosage form and improving the composition by finding out the minimum possible dosage that will provide effective control of the diseases. In this context the bio-availability of a particular drug for treating the condition is being used for the development of an effective and inexpensive drug.

In the medical field, generally complex compositions are being used for treating many of the ailments mentioned above. In such compositions, it is known to use certain herbs either in combination or individually for enhancing the therapeutic effect of the active drug. There are many reports in which such drugs are combined with other drugs to increase the potency and therapeutic efficacy of the drug. It is not clearly understood as to whether these herbs have inherent properties to cure a variety of diseases or they play a role other than aiding to cure the disease.

Quite a number of studies have been conducted to determine this. Dutt U. C. & King G. in their paper published in Materia Medica of Hindus, Calcutta (1900) have mentioned compositions containing those herbs. Laksmipathi A. their paper titled "one hundred useful drug" in the third edition of Arogya Ashram Samithi, Madras (1946) has reported that these herbs are useful in correcting the balance of Kapha, Vata & Pitta, which according to experts of Ayurveda, are the three humors of the body, the imbalance of which, is responsible for causing diseases. Bose K. G. in their paper published in Pharmacopia Indica, Calcutta, 1928, has justified the property of long pepper for increasing efficacy of Vasaka as an anti-asthmatic agent.

Studies have been made on a scientific basis for ascertaining the purpose for the extensive use of herbs, particularly belonging to the Trikatu Group. In their paper, published in Indian Drugs, 1982, (12), 476–479 Usha Zutshi et al, have reported the effect of Trikatu as a whole on vasicine resulting in enhanced bio-availability of the drug to a great extent. They have also observed that Piper longum and Piper nigrum are almost equally effective whereas ginger (Zingiber-Officinialis) alone has no significant effect.

In the Indian Patent application No. 1232/DEL/89 of Council of Scientific & Industrial Research New Delhi, India, a process has been described and claimed, in which piperine is used in combination with a known anti-tuberculosis and/or anti-leprosy drugs for the treatment of tuberculosis and/or leprosy, as such a combination imparts synergistic effect on the resultant composition resulting in the increased therapeutic efficacy to the anti-tuberculosis and/or anti-leprosy drugs.

Piperine, (E.E.) 1-[5,3-benzodioxyl-5-yl)-1-oxo-2,4-pentadieny]-piperidine, of the formula (1) shown in the drawing accompanying this specification is the main constituent of many Piper species. It is mostly obtained from Piper longum (3–5%) or Piper nigrum (3–9%) which are cultivated on a large scale in India and therefore readily available.

Piperine forms monoclinic prisms from ethanol mp 130° C. It is tasteless at first but induces burning sensation after a few seconds. It is neutral to litmus (pKa 12.22). It is soluble in benzene, chloroform, ether, ethyl acetate, dichloromethane, alcohol, acetic acid and insoluble in water, and petroleum ether. On alkaline hydrolysis it furnishes a base piperidine and the acid viz. piperic acid, mp 216° C.

IR (KBr): 2930, 1633, 1610, 1580, 1510, 1440, 1250, 1190, 1130, 1030, 995, 930, 842 cm −1.

1H NMR, CDCl$_3$ ref TMS: 1.62 (6H, bs,3×CH$_2$, 3.49 (4H, bs, 2×NCH2), 5.92 (2H, s,O—CH2—O), 6.38(d,J=15Hz, —C—C=C—) , 6.72–6.92 (6H,m, 3 olefinic & 3 Ar-H), 7.25–7.51 (1H,m, —C—C=C—).

13CNMR (CDC13): 138.4 (C-1), 113.0(C-2), 155.5(C-3), 155.5(C-4) 115.0 (C-5),129.B(C-6),145.4(C-7), 132.6 (C-B, 149.6 (C-9), 127.5 (C-10), 172.6(C-11), 50.8(C-1), 33.3 (C-2'), 31.9. (C-3'), 33.3 (C-4'), 53.B (C-5'), 10B.6 (C-6').

MS (%): M$^+$ 285 (13.6), 200 (100),172 (42.5), 142 (31.0), 114 (75.1), 84 (32.51).

Piperine can be isolated from oleo-resin of Piper nigrum (Black pepper) or Piper longum (long pepper). The powdered fruits of the plant (P.nigrum) are extracted with dichloromethane at room temperature with stirring for 12 hrs. The extract is filtered, concentrated in vacuum and the residue is subjected to purification on an alumina column. Pure piperine can be obtained by crystallization from ethanol. Piperine can also be obtained directly from the crude residue in lesser amounts by extraction with alcohol, filtration and successive crystallization.

On the basis of the disclosure made in the above said application for patent (Indian application 1232/DEL/89), research was continued to find out the reason for the synergistic effect of piperine with the anti-tuberculosis and/or anti-leprosy drugs.

As a result of the inventors' sustained research work, the inventors have found that the reason for such selective behavior of piperine is attributed to the following:

i) Synergistic property to increase the absorption of certain drugs; the invention is of particular use in respect of absorption of such drug through the membranes of the gastro-intestinal tract of the human body.

ii) Its role to retain certain drugs when combined with it in the human body for a longer period of time without allowing the drug to be eliminated from the body.

iii) Its property to increase the binding of the serum proteins and thereby retaining the major part of the drug combined with it in the body for a longer period of time.

iv) Its property to stimulate the natural immune mechanism of the body so as to enhance the production of antibodies against microbial infections.

Based on the above mentioned findings the inventors continued their research to find out the effect of piperine on the increase and/or modification of the bio-availability of a drug when piperine is combined with the drug. Accordingly, the inventors have tried the combination of piperine of the formula

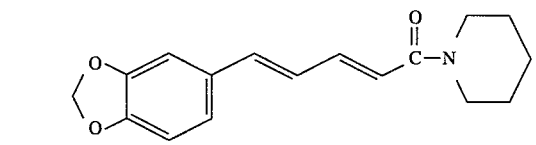

with antimicrobial agents, antiprotozoal agents, anthelmintic agents, and cardiovascular, central nervous system, non-steroid anti-inflammatory, respiratory, antihistaminics, prokinetic drugs, corticosteroids, steroid hormones, oral vaccines, haeminatics, vitamins, antiulcer drugs, muscle relaxants and anticancer drugs.

The inventors' research work has revealed that the synergistic effect of the combination of piperine is not only with anti-tuberculosis and anti-leprosy drugs. The effect is non-uniform and highly selective. The effect also produces synergistic activity in increasing the bio-availability of certain other selective drugs.

The inventors have now found that due to the synergistic effect, the bio-availability of the drugs mentioned below are also increased when these drugs are combined with piperine.

1. Antimicrobial agents such as:
    Ciprofloxacin
    Pefloxacin
    Ofloxacin
    Norfloxacin
    Phenoxymethyl penicillin
    Ampicillin
    Amoxycillin
    Cloxacillin
    Erythromycin
    Roxithromycin
    Azithromycin
    Cephalexin
    Cefadroxil
    Cerfuoxime axetil
    Cefixime
    Co-trimoxazole
    Acyclovir
    Cefaclor
    Clofazimine
    Fluconazole
    Griseofulvin
    Ketoconazole
2. Antiprotozoal agents such as:
    Metronidazole
    Tinidazole
    Quinine
    Chloroquine
    Primaquine
    Sulfadoxine+Pyrimethamine
3. Anthelmintic agents such as:
    Mebendazole in H.cyst
4. Cardiovascular drugs such as:
    Amlodipine
    Diltiazem
    Atenolol
    Lisinopril
    Lovastatin
    Gemfibrozil
    Nifedipine
    Enalapril
    Propanolol
5. Drugs acting on Central Nervous System such as:
    L-dopa
    Buspirone
    Dextropropoxyphene
    Pentazocine
    Morphin derivatives
    Diazepam
    Lorazepam
    Alprazolam
    Haloperidol
    Chlorpromazine
    Thioridazine
6. Non-steroid Anti-inflammatory Drugs such as:
    Diclofenac
    Ketorolac
    Piroxicam
    Ibuprofen
    Indomethacin
    Naproxen
7. Drugs used in treatment of Respiratory disorders such as:
    Solbutamol
    Terbutaline
    Theophylline
    Bromhexine
8. Antihistaminics such as:
    Astemizole
    Terfenadine
    Loratadine
9. Prokinetic drugs such as:
    Metoclopramide
    Domperidone
    Cisapride
10. Corticosteroids such as:
    Prednisolone
    Dexamethasone
    Betamethasone
11. Steroid hormones such as:
    Stanazolol
    Oral Contraceptives
12. Vaccines such as:
    Oral polio
13. Haematinics/Vitamins such as:
    Ferrous/Ferric Containing drugs, Multivitamin preparations.
14. Antiulcer drugs such as:
    Omeprazole
    Ranitidine
    Femotidine etc.
15. Central muscle relaxants such as:
    Carisoprodol
    Chlormezanone
16. ANTI-CANCER DRUGS:
    (i) ALKYLATING AGENTS such as:
    Mechlorthiamine
    Cyclophosphamide
    Ifosamide
    Chlorambucil
    Hexamethylmelamine
    Thiotepa
    Busulfan
    Carmustine
    Lomustine
    Semustine Streptozotocin
Decarbazine
(ii) ANTIMETABOLITE such as:
Methotrexate
5-Flurourecil
Floxuridine
Cytosine arabinoside
6-Mercaptopurine
Thioguanine
Pentostatin
(iii) NATURAL PRODUCTS such as:
Vincristine
Vinblastin
Etoposide
Teniposide
Dectinimycin
Daunorubicin
Doxorubicin
Epirubicin
Idarubicin
Bleomycin
Mithramycin
Mitomycin
L- Asparaginase
Interferon Alfa
(iv) MISCELLANEOUS AGENTS such as:
Cisplatin
Crboplatin
Mitoxantrone
Hydroxyurea
Procarbazine
Mitotane
Aminoglutethimide
(v) HORMONES AND HORMONE ANTAGONISTS such as:
Prednisolone
Hydroxyprogestirone
Medroxyprogestirone
Megestrol
Diethylstilbestirole
Ethinyl estradiol
Tamoxifen
Testosterone propionate
Fluoxymesterone
Flutamide
Leuprolide The present invention also provides a process for the preparation of pharmaceutical compositions having increased therapeutic efficacy which comprises piperine of the formula

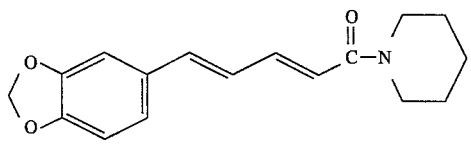

The pharmaceutical preparations are prepared by mixing a drug used in the treatment of the cardiovascular, central nervous system, gastro-intestinal tract, respiratory tract, endocrine system, genito-urinary tract or the haemopoietic system of the human body with piperine.

In a preferred embodiment of the invention, the quantity of piperine used may vary from 0.1 to 50% by weight of the drug. More preferably the amount of piperine may vary from 0.1 to 20% by weight of the drug. The amount of the drug in the composition may vary from 70 to 95% by weight of the composition. The remaining 30 to 5% of the composition is made up of piperine and as necessary pharmaceutically acceptable inert excipients, vehicles diluents and/or binding agents. Though the efficacy of the composition has more effect when piperine and the drug are administered in one single composition, the possibility of administering the required quantity of the drug and piperine separately is also envisaged according to this invention. In other words, the drug and piperine may be administered to the patient separately. However, it is preferred to use the composition as a single dosage form. It is also preferred that the composition be administered orally. If the drug and piperine are administered separately, it is also preferred that they be administered orally.

The drugs used in the composition may be any one or more of the drugs mentioned above.

Piperine as such does not have any pharmaceutical or medicinal properties. It is therefore surprising that it causes a synergistic effect in increasing the bio-availability of the drugs mentioned above.

It would be observed from the above description that piperine when mixed with the above said drugs produces synergistic effects resulting in a composition which has enhanced bio-availability of the drug and consequently helps in reducing the quantity of drug to be administered to the patient for producing the same therapeutic effect. Such an effect will avoid unnecessary administration of the drug to the patient, which will help in minimizing, reducing or eliminating whatever the adverse effect the drug might have on the patient. In other words, such a combination increases the therapeutic index of the drug.

Therefore, the combination of piperine and any one or more of the drugs mentioned above, is not a mere admixture of the ingredients employed in the process resulting in the mere aggregation of the properties of the ingredients.

The pharmaceutical composition prepared by the process of the present invention may be in any form which is usually employed for the administration of the drug for therapeutic purposes. Accordingly, the composition may be in the form of tablets, capsules, syrups, liquids suspensions, elixirs, caplets, powders, chewables, wafers, lozenges, topical preparations, patches and the like. The composition may also include flavorings, colorings and/or sweeteners.

The invention is described in detail in the examples given below which are prepared by way of illustration only and therefore should not be construed to or limit the scope of the present invention.

EXAMPLE 1

| COMPOSITION | | | |
|---|---|---|---|
| Amlodipine | — | — | 10 mg. |
| Piperine | — | — | 5 mg. |

Dosage Form: Hard gelatin capsules

PREPARATION OF FORMULATION

According to the standards and methods mentioned in pharmacopoeia, the purity of amlodipine and its potency was analyzed. It was observed that the drug was in accordance to the standards in all respects. In order to confirm and ensure the purity of piperine as a single entity, piperine was subjected to various biological assays such as physical, chemical and chromatography (TLC and HPLC).

Amlodipine and piperine were milled. The two components were blended together. They were then mixed thoroughly to a homogenous mixture by repeated sieving.

The homogenecity of five random samples of the mixture was confirmed from reproducible analysis. The formulation was then encapsulated in hard gelatin capsule in hand-operated capsule filling machine.

METHOD OF CLINICAL TRIAL

To compare the bio-availability of two formulations containing amlodipine (with and without piperine) a clinical study was conducted in 12 healthy volunteers. It was observed that addition of piperine increased blood levels of the active ingredient Amlodipine.

EXAMPLE 2

| COMPOSITION | | | |
|---|---|---|---|
| Pentazocine | — | — | 25 mg. |
| Piperine | — | — | 5 mg. |

Dosage Form: Hard gelatin capsules.

PREPARATION OF FORMULATION

Based on the pharmacopoeal methods of standardization, the analysis of pentazocine was done to confirm its purity and potency. It was demonstrated that in all respects the drug was consistent to the standards laid down in pharmacopoeia. Various methods of assays such as chemical, physical and chromatography (TLC and HPLC) were employed to confirm the purity of piperine as a single entity.

Both pentazocine and piperine were milled and were then blended together. With repeated sieving, both the components were mixed to a homogenous mixture. Five samples of mixtures were randomly selected and their homogenecity was confirmed by reproducible analysis. With the help of hand-operated capsule filling machine, the formulation was encapsulated in hard gelatin capsule.

METHOD OF CLINICAL TRIAL

A clinical trial was conducted in 12 healthy volunteers in order to compare the bio-availability of two formulations containing pentazocine (with and without piperine). It was demonstrated that incorporation of piperine increased blood levels of the active ingredient pentazocine.

EXAMPLE 3

| COMPOSITION | | | |
|---|---|---|---|
| Ranitidine | — | — | 150 mg |
| Piperine | — | — | 5 mg. |

Dosage Form: Hard gelatin capsules

PREPARATION OF FORMULATION

Based on the Pharmacopoeal methods of standardization, the analysis of ranitidine was done to confirm its purity and potency. It was demonstrated that in all respects the drug was consistent to the standards laid down in Pharmacopoeia. Various assays such as chemical, physical and chromatography (TLC and HPLC) were employed to confirm the purity of piperine as a single entity.

Both ranitidine and piperine were milled and were then blended together. With repeated sieving, both the components were mixed to a homogenous mixture. Five samples of the mixtures were randomly selected and their homogenecity was confirmed by reproducible analysis. With the help of hand-operated capsule filling machine, the formulation was encapsulated in hard gelatin capsules.

METHOD OF CLINICAL TRIAL

A clinical trial was conducted in 12 healthy volunteers, in order to compare the bio-availability of two formulations containing ranitidine (with and without piperine). It was demonstrated that incorporation of piperine increased blood levels of the active ingredient ranitidine.

EXAMPLE 4

| COMPOSITION | | | |
|---|---|---|---|
| Theophylline | — | — | 150 mg. |
| Piperine | — | — | 5 mg. |

Dosage Form: Hard Gelatin capsules.

PREPARATION OF FORMULATION

Pharmacopoeal methods of standardization were employed for the analysis of theophylline and to confirm its purity and potency. It was found that the drug was in consonance with the Pharmacopoeal standards in all respects. In order to assess the purity of piperine as a single entity, various methods of analysis such as physical, chemical and chromatography (including TLC and HPLC) were employed.

After milling theophylline and piperine, they were then blended together. Both the components were then mixed to a homogenous mixture with repeated sieving. Reproducible analysis was considered as a measure to confirm the homogenecity of the randomly selected five samples of the mixtures. Hand-operated capsule filling machine was used for encapsulation of the formulation in hard gelatin capsules.

METHOD OF CLINICAL TRIAL

Bio-availability of two formulations containing theophylline (with and without piperine) were compared in 12 healthy volunteers, by conducting a controlled-clinical trial. It was found that addition of piperine enhanced blood levels of the active ingredient theophylline.

EXAMPLE 5

| COMPOSITION | | | |
|---|---|---|---|
| Prednisolone | — | — | 10 mg. |
| Piperine | — | — | 5 mg. |

Dosage Form: Hard gelatin capsules.

PREPARATION OF FORMULATION

The purity of prednisolone and its potency was analyzed to its Pharmacopoeal standards using the methods prescribed therein. The drug was found to be conforming to standards in all respects. Piperine was subjected to various physical and chemical analysis including chromatography (TLC and HPLC) in order to confirm and ensure its purity as a single entity.

Both prednisolone and piperine were milled. The two components were blended together and then mixed thoroughly to a homogenous mixture by repeated sieving. Reproducible analysis of five random samples of the mixture confirmed its homogenecity. The formulation thus obtained was encapsulated in hard-gelatin capsules in hand-operated capsule filling machines.

METHOD OF CLINICAL TRIAL

A clinical trial was carried out in 12 healthy volunteers, in order to compare the bioavailability of two formulations containing prednisolone (with and without piperine). It was observed that blood levels of the active ingredient prednisolone.

EXAMPLE 6

| COMPOSITION | | | |
|---|---|---|---|
| Ciprofloxacin | — | — | 250 mg. |
| Piperine | — | — | 5 mg. |

Dosage Form: Hard gelatin capsules

PREPARATION OF FORMULATION

Pharmacopoeal methods of standardization was employed for the analysis of Ciprofloxacin and to confirm its purity and potency. It was found that the drug was in consonance with the Pharmacopoeal standards in all respects. In order to assess the purity of piperine as a single entity, various methods of analysis such as physical, chemical and chromatography (including TLC and HPLC) were employed.

After milling ciprofloxacin and piperine, they were then blended together. Both the components were then mixed to a homogenous mixture with repeated sieving. Reproducible analysis was considered as a measure to confirm the homogenecity of the randomly selected five samples of the mixtures. Hand-operated capsule filling machine was used for encapsulation of the formulation in hard gelatin capsules.

METHOD OF CLINICAL TRIAL

Bio-availability of two formulations containing ciprofloxacin (with and without piperine) were compared in 12 healthy volunteers, by conducting a controlled-clinical trial. It was found that addition of piperine enhanced blood levels of the active ingredient ciprofloxacin.

EXAMPLE 7

| COMPOSITION | | | |
|---|---|---|---|
| Methotrexate | — | — | 10 mg. |
| Piperine | — | — | 5 mg. |

PREPARATION OF FORMULATION

The purity of methotrexate and its potency was analyzed to its Pharmacopoeal standards using the methods prescribed therein. The drug was found to be conforming to standards in all respects. Piperine was subjected to various physical, chemical analysis including chromatography (TLC and HPLC) in order to confirm and ensure its purity as a single entity.

Both methotrexate and piperine were milled. The two components were blended together and then mixed thoroughly to a homogenous mixture by repeated sieving. Reproducible analysis of five random samples of the mixture confirmed its homogenecity. The formulation thus obtained was encapsulated in hard gelatin capsules in hand-operated capsule filling machine.

METHOD OF CLINICAL TRIAL

A clinical trial was carried out in 12 healthy volunteers, in order to compare the bioavailability of two formulations containing methotrexate (with and without piperine). It was observed that addition of piperine increased blood levels of the active ingredient methotrexate.

We claim:

1. A pharmaceutical composition having increased bioavailability comprising piperine of the formula

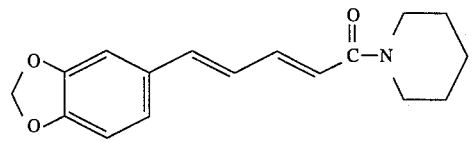

and a drug wherein the drug is an antimicrobial agent, antiprotozoal agent, anthelmintic agent, central nervous system drug, non-steroid anti-inflammatory drug, antihistaminic, prokinetic drug, corticosteroid, steroid hormone, oral vaccine, haematinic, vitamin, antiulcer drug, muscle relaxant, or anticancer drug; the amount of piperine in the composition is from 0.1 to 50% by weight of the drug and the amount of the drug is from 70 to 95% by weight of the composition.

2. A method of treating a disease or condition of the human cardiovascular system, central nervous system, gastrointestinal tract, respiratory tract, endocrine system, genito urinary tract or haemopoietic system comprising administering a pharmaceutical composition comprising piperine of the formula

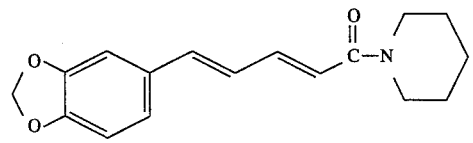

and a drug wherein the drug is an antimicrobial agent, antiprotozoal agent, anthelmintic agent, central nervous system drug, non-steroid anti-inflammatory drug, antihistaminic, prokinetic drug, corticosteroid, steroid hormone, oral vaccine, haematinic, vitamin, antiulcer drug, muscle relaxant, or anticancer drug; the amount of piperine in the composition is from 0.1 to 50% by weight of the drug and the amount of the drug is from 70 to 95% by weight of the composition.

3. A pharmaceutical composition having increased bioavailability comprising piperine of the formula

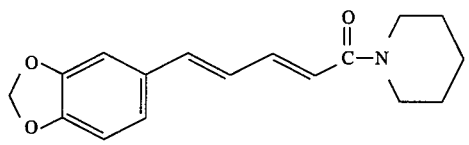

and a drug is selected from the group consisting of
Ciprofloxacin
Pefloxacin
Ofloxacin
Norfloxacin
Phenoxymethyl penicillin
Ampicillin
Amoxycillin
Cloxacillin
Erythromycin
Roxithromycin
Azithromycin
Cephalexin
Cefadroxil
Cerfuoxime axetil
Cefixime
Co-trimoxazole
Acyclovir
Cefaclor
Clofazimine
Fluconazole
Griseofulvin and
Ketoconazole,
the amount of piperine in the composition is from 0.1 to 50% by weight of the drug and the amount of the drug is from 70 to 95% by weight of the composition.

4. A pharmaceutical composition having increased bioavailablity comprising piperine of the formula

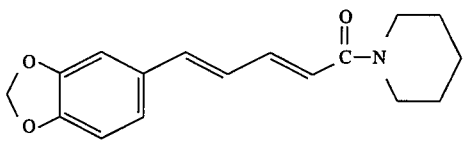

and a drug wherein the drug is selected from the group consisting of
Solbutamol
Terbutaline and
Bromhexine,
the amount of piperine in the composition is from 0.1 to 50% by weight of the drug and the amount of the drug is from 70 to 95% by weight of the composition.

5. A pharmaceutical composition having increased bioavailability comprising piperine of the formula

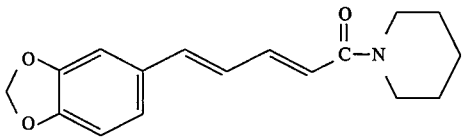

and a drug wherein the drug is selected from the group consisting of
Amlodipine
Diltiazem
Atenolol
Lisinopril
Lovastatin
Gemfibrozil
Nifedipine and
Enalapril,
the amount of piperine in the composition is from 0.1 to 50% by weight of the drug and the amount of the drug is from 70 to 95% by weight of the composition.

6. A method of treating a disease or condition of the human cardiovascular system, central nervous system, gastrointestinal tract, respiratory tract, endocrine system, genito urinary tract or haemopoietic system comprising administering a pharmaceutical composition comprising piperine of the formula

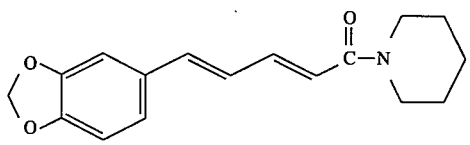

and a drug wherein the drug is selected from the group consisting of
Solbutamol
Terbutaline and
Bromhexine,
the amount of piperine in the composition is from 0.1 to 50% by weight of the drug and the amount of the drug is from 70 to 95% by weight of the composition.

7. A method of treating a disease or condition of the human cardiovascular system, central nervous system, gastrointestinal tract, respiratory tract, endocrine system, genito urinary tract or haemopoietic system comprising administering a pharmaceutical composition comprising piperine of the formula

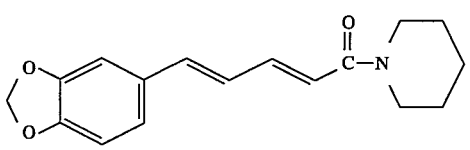

and a drug wherein the drug is selected from the group consisting of
Ciprofloxacin
Pefloxacin
Ofloxacin
Norfloxacin
Phenoxymethyl penicillin
Ampicillin
Amoxycillin
Cloxacillin
Erythromycin
Roxithromycin
Azithromycin
Cephalexin
Cefadroxil
Cerfuoxime axetil
Cefixime Co-trimoxazole
Acyclovir
Cefaclor
Clofazimine
Fluconazole
Griseofulvin and
Ketoconazole, the amount of piperine in the composition is from 0.1 to 50% by weight of the drug and the amount of the drug is from 70 to 95% by weight of the composition.

8. A method of treating a disease or condition of the human cardiovascular system, central nervous system, gastrointestinal tract, respiratory tract, endocrine system, genito urinary tract or haemopoietic system comprising administering a pharmaceutical composition comprising piperine of the formula

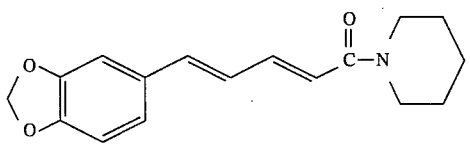

and a drug wherein the drug is selected from the group consisting of

Amlodipine
Diltiazem
Atenolol
Lisinopril
Lovastatin
Gemfibrozil
Nifedipine and
Enalapril the amount of piperine in the composition is from 0.1 to 50% by weight of the drug and the amount of the drug is from 70 to 95% by weight of the composition.

9. A composition according to claim 1, wherein the amount of piperine in the composition is from 0.1 to 20% by weight of the drug.

10. A composition according to claim 1, wherein the drug is amlodipine, diltiazem, atenolol, enalapril, pentazocine, alprazolam, fluoxitine, omeprazole, ranitidine, femotidine, salbutamol, terbutaline, bromhexine, roxithromycine, prednisolone, dexamethasone, estrogen, stanazolol, frusamide, dicyclomine or ciprofloxacin.

11. A composition according to claim 1, in the form of a tablet, capsule, syrup, suspension, liquid, elixir, caplet, powder, chewable, water or lozenge.

12. A method according to claim 2, wherein the drug is amlodipine, diltiazem, atenolol, enalapril, pentazocine, alprazolam, fluoxitine, omeprazole, ranitidine, femotidine, salbutamol, terbutaline, bromhexine, roxithromycine, prednisolone, dexamethasone, estrogen, stanazolol, frusamide, dicyclomine or ciprofloxacin.

13. A method according to claim 2, wherein the amount of piperine in the composition is from 0.1 to 20% by weight of the drug.

* * * * *